(12) United States Patent
Smith et al.

(10) Patent No.: US 9,302,065 B2
(45) Date of Patent: Apr. 5, 2016

(54) PATIENT INTERFACE DEVICE WITH ADJUSTABLE HEADGEAR AND FRAME

(75) Inventors: David W. Smith, Oakmont, PA (US); Gregory John Jablonski, Butler, PA (US); Derrick Blake Andrews, Merkleton, PA (US); Harold Allen Lockhart, Mt. Pleasant, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 790 days.

(21) Appl. No.: 13/503,102

(22) PCT Filed: Aug. 31, 2010

(86) PCT No.: PCT/IB2010/053905
§ 371 (c)(1),
(2), (4) Date: Apr. 20, 2012

(87) PCT Pub. No.: WO2011/048510
PCT Pub. Date: Apr. 28, 2011

(65) Prior Publication Data
US 2012/0204878 A1   Aug. 16, 2012

Related U.S. Application Data

(60) Provisional application No. 61/254,272, filed on Oct. 23, 2009.

(51) Int. Cl.
*A61M 16/06* (2006.01)
*A61M 16/00* (2006.01)

(52) U.S. Cl.
CPC ........... *A61M 16/0683* (2013.01); *A61M 16/06* (2013.01); *A61M 16/0672* (2014.02); *A61M 2210/0618* (2013.01)

(58) Field of Classification Search
CPC . A61M 16/00; A61M 16/04; A61M 16/0488; A61M 16/06; A61M 16/0683; A61M 25/00; A61M 25/02–25/04; A61M 16/0051; A61M 16/0465; A61M 16/0493; A61M 16/0497; A61M 16/0666; A61M 16/0672; A61M 16/10; A61M 16/16; A61M 16/209; A61M 2025/0206; A61M 2025/022; A61M 2025/0226; A61M 2025/024; A61M 2025/026; A61M 2025/028; A61M 2205/183; A61M 2205/42; A61M 2210/0618; A61M 2230/005; B01F 13/00; B01F 13/002; B01F 3/04; B01F 3/04007; F16K 15/14; F16K 15/141; F16K 17/02; F16K 17/04; F16K 17/0446; F16K 37/00; Y10S 128/26; Y10S 128/911; Y10S 128/912; Y10S 261/65; Y10T 137/7879; Y10T 137/8326
USPC ............ 128/200.24, 202.27, 205.25, 206.21, 128/206.27, 207.11, 207.14, 207.17, 207.18
See application file for complete search history.

(56) References Cited

U.S. PATENT DOCUMENTS 3,834,682 A * 9/1974 McPhee ........................ 261/123
5,438,979 A * 8/1995 Johnson et al. .......... 128/207.18
(Continued)

FOREIGN PATENT DOCUMENTS

| EP | 2022528 A2 | 11/2009 |
|---|---|---|
| WO | WO2008007985 A1 | 1/2008 |
| WO | WO2009059353 A1 | 5/2009 |

OTHER PUBLICATIONS
U.S. Appl. No. 11/799,802, filed May 3, 3007.

*Primary Examiner* — Annette Dixon
(74) *Attorney, Agent, or Firm* — Michael W. Haas

(57) ABSTRACT

A patient interface device includes a main frame and a headgear. The main frame includes a central support portion for supporting a cushion component and first and second arms extending from the central support portion. The headgear includes a support portion, and first and second straps extending therefrom. The first strap has a first pocket and the second strap has a second pocket, wherein the first arm is received and moveable within the first pocket along a longitudinal axis of the first strap and the second arm is received and moveable within the second pocket along a longitudinal axis of the second strap. The headgear also includes first and second fastening mechanisms for securing the headgear to the main frame, holding the first arm in a selected position within the first pocket and holding the second arm in a selected position within the second pocket.

8 Claims, 3 Drawing Sheets

(56) References Cited

U.S. PATENT DOCUMENTS 7,318,437 B2 * 1/2008 Gunaratnam et al. ... 128/206.11
2004/0226566 A1 11/2004 Gunaratnam
2006/0196511 A1 9/2006 Lau et al.
2008/0302366 A1 12/2008 McGinnis

* cited by examiner

PATIENT INTERFACE DEVICE WITH ADJUSTABLE HEADGEAR AND FRAME

CROSS-REFERENCE TO RELATED APPLICATIONS

This patent application claims the priority benefit under 35 U.S.C. §371 of international patent application no. PCT/IB2010/053905, filed Aug. 31, 2010, which claims the priority benefit under 35 U.S.C. §119(e) of U.S. Provisional Application No. 61/254,272 filed on Oct. 23, 2009, the contents of which are herein incorporated by reference.

BACKGROUND OF THE INVENTION

1. Field of the Invention

The present invention relates to patient interface devices, and, in particular, to a patient interface device having an adjustable, integrated headgear and frame for allowing the fit of the patient interface device to be selectively adjusted.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a cushion component on the face of a patient. The cushion component may be, without limitation, a nasal mask that covers the patient's nose, a nasal cushion having nasal prongs that are received within the patient's nares, a nasal/oral mask that covers the nose and mouth, or full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head. Because such patient interface devices are typically worn for an extended period of time, it is important for the headgear to maintain the cushion component of the device in a tight enough seal against the patient's face without discomfort.

For patient interface devices, a key engineering challenge is to balance patient comfort against stability of the device as well as minimize unintentional gas leakage at the patient-cushion interface. As a patient changes sleeping positions through the course of the night, the mask portions of patient interface devices may become dislodged, and the seal against the patient's may be broken. A dislodged mask portion can be stabilized by the increasing strapping force provided by the headgear, but increased strapping force tends to reduce patient comfort. This design conflict is further complicated by the widely varying facial geometries that a given patient interface device design needs to accommodate. Such wide variation in facial geometry is demonstrated in Table 1 below (source: PeopleSize2008 database, OpenErgonomics Ltd.).

TABLE 1

|  | 5% US population Min (mm) | 95% US population Max (mm) | Variation (mm) |
| --- | --- | --- | --- |
| Nose Tip Depth | 15 | 23 | 8 |
| Nose Length | 44 | 57 | 13 |
| Eye corner to back of head | 151 | 184 | 33 |
| Nose base to back of head | 182 | 216 | 34 |
| Cheekbone width | 126 | 150 | 24 |
| Head Breadth | 140 | 167 | 27 |

To further complicate this issue, individual tolerances for comfort also vary widely. For instance, given the same level of mechanical pressure on a specific area of the face, one person may develop significant marks, blisters, or open sores, while another person may feel no effects at all.

One known patient interface device is the Swift LT available from ResMed Inc. In that device, a plastic stiffener is fixedly stitched to the fabric headgear extensions. This allows for stability of the mask, but does not allow for relative motion between the fabric and the stiffener. Therefore, a patient cannot properly adjust this to their specific needs.

Another known patient interface device is the ComfortGel nasal mask available from Philips Respironics. That device includes four attachment points between the fabric headgear and the plastic mask that allow for relative motion between the fabric headgear and the plastic mask. However, in this device, the mask is free to move in many degrees of freedom, which can lead to instability (especially for a pillows style masks).

SUMMARY OF THE INVENTION

In one embodiment, a patient interface device is provided that includes a main frame having a central support portion for supporting a cushion component and a first arm and a second arm extending from the central support portion, and a headgear. The headgear includes a support portion, a first strap extending from a first side of the support portion and a second strap extending from a second side of the support portion. The first strap has a first pocket and the second strap has a second pocket, wherein the first arm is received and moveable within the first pocket along a longitudinal axis of the first strap and the second arm is received and moveable within the second pocket along a longitudinal axis of the second strap. Also, the headgear includes a first fastening mechanism for securing the headgear to the main frame and holding the first arm in a selected position within the first pocket and a second fastening mechanism for securing the headgear to the main frame and holding the second arm in a selected position within the second pocket.

The first fastening mechanism may include a first strap loop provided on the first arm that receives an end of the first strap therethrough, and the second fastening mechanism may include a second strap loop provided on the second arm that receives an end of the second strap therethrough. The first fastening mechanism may further include a first hook and loop fastener system provided on the first strap for securing the end of the first strap to an exterior of the first strap after the first strap is inserted through the first strap loop, and the second fastening mechanism may further include a second hook and loop fastener system provided on the second strap for securing the end of the second strap to an exterior of the second strap after the first strap is inserted through the second strap loop.

In an exemplary embodiment, the headgear is made of a soft, flexible material, such as fabric, and the main frame is made of a stiff material, such as a thermoplastic material.

A method of fitting a patient interface device is also provided. The method includes receiving the patient interface device, wherein the patient interface device includes: (i) a main frame, the main frame having a central support portion for supporting a cushion component and a first arm and a second arm extending from the central support portion; and (ii) a headgear, the headgear including a support portion, a first strap extending from a first side of the support portion and a second strap extending from a second side of the support portion, the first strap having a first pocket and the second strap having a second pocket, inserting the first arm into the first pocket, inserting the second arm into the second pocket, moving the first arm within the first pocket along a longitudinal axis of the first strap to a first selected position within the first pocket and securing the headgear to the main frame and securing the first arm in the first selected position, and moving the second arm within the second pocket along a longitudinal axis of the second strap to a second selected position within the second pocket and securing the headgear to the main frame and securing the second arm in the second selected position.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1:
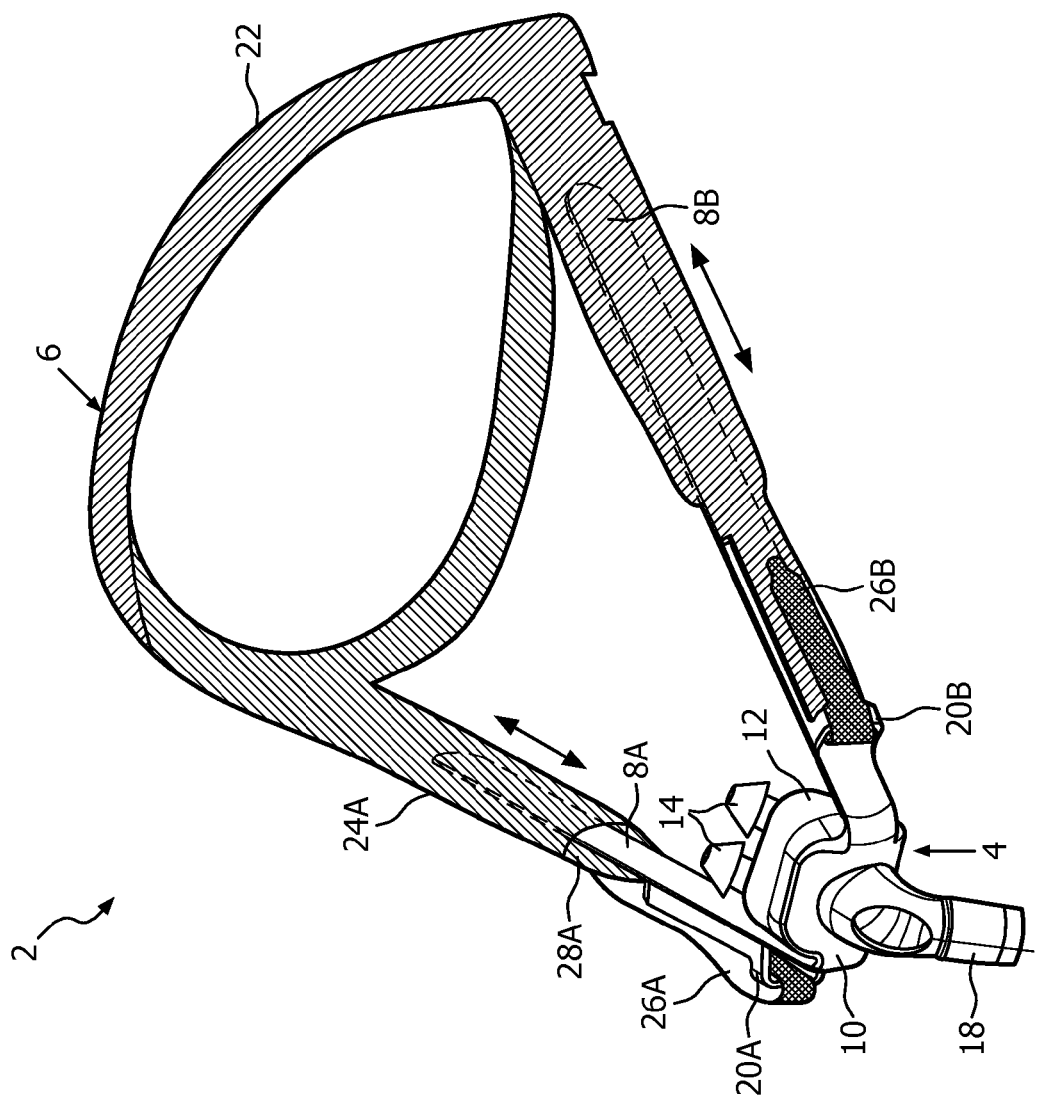
FIG. 1 is an isometric view of a patient interface device according to one particular embodiment of the present invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As employed, herein, the statement that two or more parts or components are "coupled" together shall mean that the parts are joined or operate together either directly or through one or more intermediate parts or components. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

FIG. 1 is an isometric view of a patient interface device 2 according to one particular embodiment of the present invention. Patient interface device 2 includes a main frame 4 and headgear 6. Main frame 4 is preferably made of a stiff material such as a thermoplastic, and headgear is preferably made of a soft, flexible material such as a fabric material. As described in greater detail herein, main frame 4 is coupled to headgear 6 in a manner that allows main frame 4 to be selectively moved relative to headgear 6 in order to adjust the fit of patient interface device 2.

Figure 2:
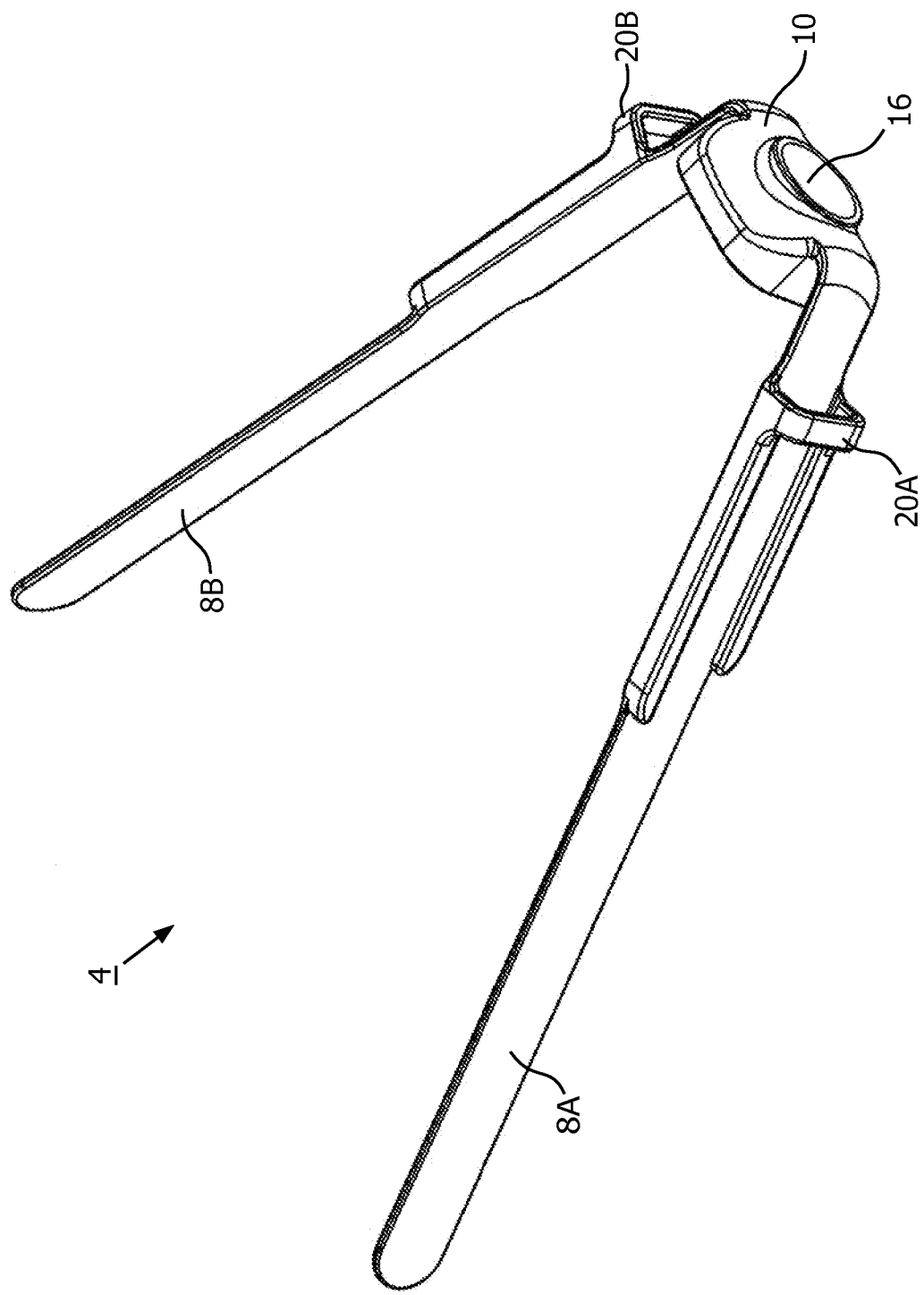
FIG. 2 is an isometric view of the main frame of the patient interface device of FIG. 1.

FIG. 2 is an isometric view of main frame 4. Main frame 4 includes arms 8A and 8B and a cushion support portion 10. Arms 8A and 8B extend outwardly from cushion support portion 10 of main frame 4 and serve as stiffening elements for patient interface device 2. Cushion support portion 10 receives and holds a nasal cushion 12 having nasal prongs 14. It is to be understood that nasal cushion 12 having nasal prongs 14 is but one example of a cushion component that may be used with main frame 4, and that other cushion components, such as, without limitation, a nasal/oral mask, may also be used. Cushion support portion 10 includes an opening 16 to which there is attached a fluid coupling device 18, such as a swivel conduit as shown, for carrying fluid, such as a breathing gas, to nasal cushion 12 from an external gas source (not shown), such as a blower or other suitable device. It is to be understood that the present invention contemplates a variety of different fluid coupling devices 18 that could be attached, either permanently or selectively, to opening 16 to carry fluid to or from nasal cushion 12.

Arm 8A of main frame 4 includes a strap loop 20A and arm 8B of main frame 4 includes a strap loop 20B. Strap loops 20A and 20B are structured to cooperate with headgear 6 as described below.

Figure 3:
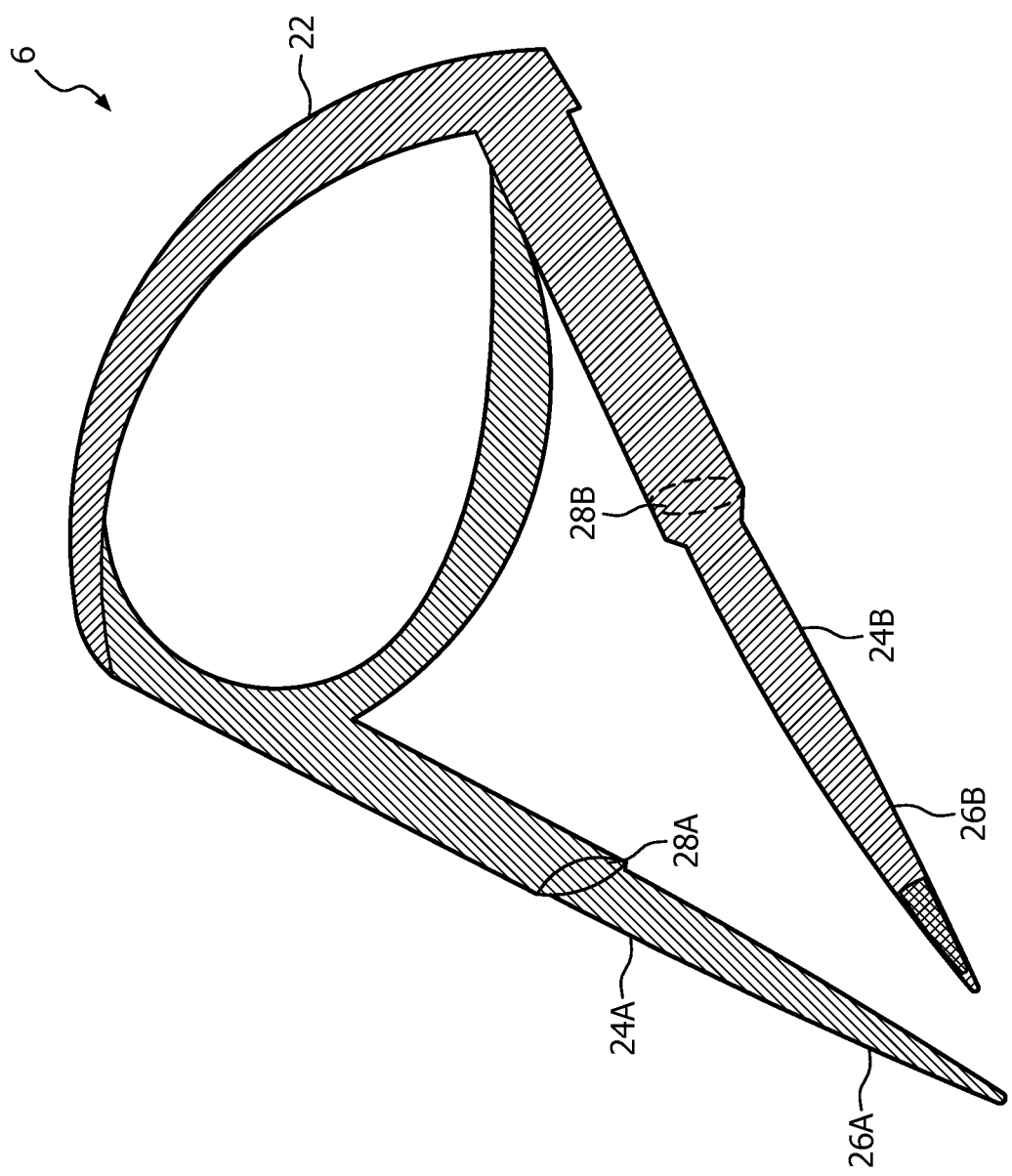
FIG. 3 is an isometric view of the headgear of the patient interface device of FIG. 1.

Referring to FIG. 3, headgear 6 includes a rear support portion 22 that is structured to engage the back of the patient's head. Headgear 6 also includes strap 24A and strap 24B extending from rear support portion 22. Strap 24A includes an end portion 26A and has a pocket 28A formed therein, with the entrance to pocket 28A being on the inner side of strap 24A as seen in FIG. 3. Similarly, strap 24B includes an end portion 26B and has a pocket 28B formed therein, with the entrance to pocket 28B being on the inner side of strap 24B as seen in FIG. 3.

When patient interface device 2 is assembled, arm 8A of main frame 4 is inserted into pocket 28A and arm 8B of main frame 4 inserted into pocket 28B as seen in FIG. 1. Arms 8A and 8B are able to move freely within pockets 28A, 28B along the respective longitudinal axes of straps 24A and 24B as shown by the arrows in FIG. 1. As will be appreciated, the position of arms 8A and 8B within pockets 28A, 28B will determine the size of patient interface device 2.

A fastening system is provided for securing main frame 4 to headgear 6 once the desired position of arms 8A and 8B within pockets 28A, 28B is determined and achieved. In the illustrated embodiment, fastening system 18 is a hook and loop fastener, such as VELCRO®. In particular, the exterior of each of strap 24A and 24B includes a loop fastener portion, and a corresponding hook fastener portion is provided on the exterior of each of end portions 26A, 26B. Thus, strap 24A may be threaded through strap loop 20A and then bent back on itself to adhere the hook fastener portion of end portion 26A of strap 24A to the loop fastener portion provided on the exterior of strap 24A. Similarly, strap 24B may be threaded through strap loop 20B and then bent back on itself to adhere the hook fastener portion of end portion 26B of strap 24B to the loop fastener portion provided on the exterior of strap 24B. Of course, the present invention contemplates that the fastening system may use other forms of connection other than hook and loop fasteners such as snaps or buckles.

Thus, in the embodiment just described, the tension of straps 24A and 24B may be adjusted for a specific facial anatomy and comfort level. As the tension of straps 24A and 24B is adjusted, straps 24A, 24B move through strap loops 20A, 20B. This action will tend to pull main frame 4 further into the pockets 28A and 28B when applying tension, and allow main frame 4 to extend from pockets 28A and 28B when tension is released. In either case, main frame 4, through arms 8A and 8B, is always providing support around the patient's head, and the soft cushioning sections of headgear 6 are always in contact with the patient's skin. The present invention is thus advantageous as it allows for both stability and adjustability by allowing arms 8A and 8B to slide longitudinally/axially within pockets 28A and 28B while at the same time restricting movement of arms 8A and 8B in other directions.

Furthermore, ease of use is another advantage of present invention. By providing the fastening system by way of cooperation between end portions 26A and 26B and strap loops 18A and 18B, the primary means of adjustment is near the cheeks of the patient. This is a natural position for a primary adjustment and does not require complex hand motions or ranges of motion from the patient.

In short, in the present invention, the position of main frame 4 relative to headgear 6 may be selectively altered and secured as just described in order to allow the size of patient interface device 2 to be selectively adjusted by the patient or a caregiver to optimize the comfort and stability of patient interface device 2 for the patient's particular facial anatomy. This adjustment mechanism is particularly advantageous as it allows for a broad range of motion for the main dimension of patient interface device 2 to be adjusted by the patient. In addition, as noted elsewhere herein, arms 8A and 8B of main frame 4, which are not permanently affixed to headgear 6, extend far along the side of the patient's head when patient interface device 2 is worn and act as stiffening elements which also assist in optimizing the comfort and stability of patient interface device 2.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
a main frame comprising a central support portion for supporting a cushion component on a first side of the central support portion, a first arm extending from a first side of the central support portion, and a second arm extending from a second side of the central support portion, the central support portion having a central opening extending therethrough;
a fluid coupling device structured to be coupled to the central support portion at a second side of the central support portion opposite the first side of the central support portion in a manner wherein the fluid coupling device is fluidly coupled to the central opening to enable fluid to be carried to or from the cushion component through the fluid coupling device and the central opening; and
a headgear including a support portion made of a soft, flexible material, a first strap made of the soft, flexible material and extending from a first side of the support portion, and a second strap made of the soft, flexible material extending from a second side of the support portion, the first strap having a first pocket formed by the soft, flexible material and the second strap having a second pocket formed by the soft, flexible material, wherein a first end portion of the first arm is received within the first pocket in a manner wherein the first arm is moveable along a longitudinal axis of the first strap and an entirety of the first end portion of the first arm is held within and surrounded and covered by the soft, flexible material such that movement of the first end portion of the first arm is restricted in directions other than along the longitudinal axis of the first strap, and wherein a first end portion of the second arm is received within the second pocket in a manner wherein the second arm is moveable along a longitudinal axis of the second strap and an entirety of the first end portion of the second arm is held within and surrounded and covered by the soft, flexible material such that movement of the first end portion of the second arm is restricted in directions other than along the longitudinal axis of the second strap, the patient interface device including a first fastening mechanism for securing the headgear to the main frame and holding the first arm in a selected position within the first pocket and a second fastening mechanism for securing the headgear to the main frame and holding the second arm in a selected position within the second pocket, wherein the first fastening mechanism includes a first strap loop provided on the first arm, the first strap loop receiving an end of the first strap therethrough, wherein the second fastening mechanism includes a second strap loop provided on the second arm, the second strap loop receiving an end of the second strap therethrough.

2. The patient interface device of claim 1, the first fastening mechanism further including a first hook and loop fastener system provided on the first strap for securing the end of the first strap to an exterior of the first strap after the first strap is inserted through the first strap loop, and the second fastening mechanism further including a second hook and loop fastener system provided on the second strap for securing the end of the second strap to an exterior of the second strap after the first strap is inserted through the second strap loop.

3. The patient interface device of claim 1, wherein the main frame is made of a stiff material.

4. The patient interface device of claim 3, wherein the main frame is made of a thermoplastic material.

5. The patient interface device of claim 1, wherein the soft, flexible material is a fabric material.

6. A method of fitting a patient interface device, comprising:
providing a patient interface device comprising: (i) a main frame comprising a central support portion for supporting a cushion component on a first side of the central support portion, a first arm extending from a first side of the central support portion, and a second arm extending from a second side of the central support portion, the central support portion having a central opening extending therethrough, (ii) a fluid coupling device structured to be coupled to the central support portion at a second side of the central support portion opposite the first side of the central support portion in a manner wherein the fluid coupling device is fluidly coupled to the central opening to enable fluid to be carried to or from the cushion component through the fluid coupling device and the central opening; and (iii) a headgear, the headgear including a support portion made of a soft, flexible material, a first strap made of the soft, flexible material and extending from a first side of the support portion and a second strap made of the soft, flexible material and extending from a second side of the support portion, the first strap having a first pocket formed by the soft, flexible material and the second strap having a second pocket formed by the soft, flexible material;

inserting a first end portion of the first arm into the first pocket;

inserting a first end portion of the second arm into the second pocket;

moving the first end portion of the first arm within the first pocket along a longitudinal axis of the first strap to a first selected position within the first pocket, wherein an entirety of the first end portion of the first arm is held within and surrounded and covered by the soft, flexible material such that movement of the first end portion of the first arm is restricted in directions other than along the longitudinal axis of the first strap, and securing the headgear to the main frame and securing the first end portion of the first arm in the first selected position; and moving the second arm within the second pocket along a longitudinal axis of the second strap to a second selected position within the second pocket, wherein an entirety of the first end portion of the second arm is held within and surrounded and covered by the soft, flexible material such that movement of the first end portion of the second arm is restricted in directions other than along the longitudinal axis of the second strap, and securing the headgear to the main frame and securing the first end portion of the second arm in the second selected position, wherein the securing the first end portion of the first arm in the first selected position comprises inserting a first end of the first strap through a first strap loop provided on the first arm, and wherein the securing the first end portion of the second arm in the second selected position comprises inserting a second end of the second strap through a second strap loop provided on the second arm.

7. The method according to claim 6, wherein the securing the first end portion of the first arm in the first selected position further comprises securing the first end portion of the first arm in the first selected position with a first hook and loop fastener system, and wherein the securing the first end portion of the second arm in the second selected position further comprises securing the first end portion of the second arm in the second selected position with a second hook and loop fastener system.

8. The method according to claim 6, wherein the moving and securing steps are performed after the patient interface device is donned by a patient.

* * * * *